United States Patent [19]

Shepherd

[11] 4,154,756
[45] May 15, 1979

[54] 2-SUBSTITUTED-4'-(MONOALKYLAMINO)-ACETOPHENONES

[75] Inventor: Robert G. Shepherd, South Nyack, N.Y.

[73] Assignee: American Cyanamid Company, Stamford, Conn.

[21] Appl. No.: 860,915

[22] Filed: Dec. 15, 1977

[51] Int. Cl.² .................. C07C 101/78; C07C 103/28; C07C 121/78; C07C 147/12
[52] U.S. Cl. ............................ 260/465 D; 260/465 E; 260/558 A; 260/558 S; 260/559 A; 260/559 T; 260/562 B; 260/574; 260/577; 260/593 H; 260/658 R; 424/304; 424/309; 424/319; 424/324; 424/330; 548/341; 560/12; 560/16; 560/19; 560/41; 560/45; 560/47; 560/48; 562/426; 562/430; 562/433; 562/450; 562/452

[58] Field of Search ............... 260/465 D, 465 E, 577, 260/518 R, 558 A, 558 S; 560/19, 12, 16, 41; 562/426, 430, 433, 450

[56] References Cited

U.S. PATENT DOCUMENTS

| | | | |
|---|---|---|---|
| 2,563,376 | 8/1951 | Schenck | 260/465 E |
| 2,905,679 | 9/1959 | Brockman, Jr. et al. | 260/465 D X |
| 3,197,488 | 7/1965 | Braunworth et al. | 560/51 X |
| 3,284,500 | 11/1966 | Tieman | 260/465 E X |
| 3,818,072 | 6/1974 | Grisar et al. | 560/51 |
| 3,868,416 | 2/1975 | Albright et al. | 560/19 X |

*Primary Examiner*—Dolph H. Torrence
*Attorney, Agent, or Firm*—Edward A. Conroy, Jr.

[57] ABSTRACT

This disclosure describes 2-substituted 4'-(monoalkylamino)-acetophenones useful as hypolipidemic and anti-atherosclerotic agents.

21 Claims, No Drawings

2-SUBSTITUTED-4'-(MONOALKYLAMINO)-ACETOPHENONES

BRIEF SUMMARY OF THE INVENTION

This invention relates to new organic compounds and, more particularly, is concerned with novel 2-substituted 4'-(monoalkylamino)acetophenones which may be represented by the following structural formula:

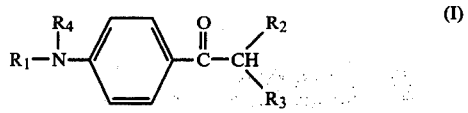

and enol tautomers thereof, wherein $R_1$ is an unbranched or branched alkyl group of the formula $C_nH_{2n+1}$ wherein n is an integer from 8 to 19, inclusive; $R_2$ is selected from the group consisting of cyano, carbamoyl, carboxyl, alkoxycarbonyl, alkylsulfonyl, alkylsulfinyl, arylsulfonyl, arylsulfinyl, lower alkanoyl, aroyl, alkoxycarbonylalkyl, and carboxyalkyl; $R_3$ is selected from the group consisting of hydrogen, cyano, alkylcarbamoyl, alkoxycarbonyl, alkylsulfonyl, alkylsulfinyl, arylsulfonyl, arylsulfinyl, lower alkanoyl, aroyl, alkoxycarbonylalkyl and carboxyalkyl; and $R_4$ is hydrogen or a group convertible in vivo thereinto such as methyl, ethyl, carboxymethyl, lower alkanoyl ($C_1$–$C_6$), or succinyl.

Suitable alkoxycarbonyl groups contemplated by the present invention are those having 2-5 carbon atoms such as, for example, methoxycarbonyl, ethoxycarbonyl, isopropoxycarbonyl, n-butoxycarbonyl, etc. Alkylsulfonyl is exemplified by methanesulfonyl, ethanesulfonyl, n-propanesulfonyl, etc. Suitable alkylsulfinyl are methanesulfinyl, ethanesulfinyl, etc. Appropriate aroyl groups may be benzoyl, 4-carboxybenzoyl, 3-nitrobenzoyl, 3,4-dimethylbenzoyl, 2-fluorobenzoyl, 4-methoxybenzoyl, while suitable lower alkanoyl groups may be acetyl, propionyl, butyryl, etc. Alkoxycarbonylalkyl groups are selected from the formula —$(CH_2)_x$COOR where x is an integer from 1 to 4 and R is alkyl having up to 4 carbon atoms. Carboxyalkyl is selected from the same formula where R is hydrogen. The novel compounds of the present invention may exist partly or completely in varous enolic forms corresponding to the keto form shown in formula (I) and this invention embraces these enolic forms as well.

Suitable branched alkyl groups for the substituent Rmay be, for example, 1-methylpentadecyl, 1-ethyltetradecyl, 1-heptylnonyl, 2-ethyldodecyl, 1,4-diethyloctyl, 11-methyldodecyl, 5,5-dimethylhexyl, 4,8,12-trimethyltridecyl, 2,4,6,8-tetramethylnonyl, 1,4-dimethyl-1-ethylhexyl, 15-methylhexadecyl, 14-methylpentadecyl, 13,13-dimethyltetradecyl, 15,15-dimethylhexadecyl, and the like.

The invention also pertains to novel compositions of matter useful as anti-atherosclerotic agents and to methods of meliorating atherosclerosis by counteracting hyperlipemia and arterial plaque formation in mammals therewith; the active ingredients of said compositions of matter being the novel 2-substituted 4'-(monoalkylamino)acetophenones of the present invention. These compounds may be utilized either as the free bases or in the form of a pharmaceutically acceptable salt with an organic or inorganic acid or base. The invention also contemplates a method for lowering serum lipids and for meliorating atherosclerosis in mammals by the administration of said compounds.

BACKGROUND OF THE INVENTION

Considerable effort has been directed in recent years to obtain substances useful in counteracting the consequences of hyperlipidemia, a condition involving elevated cholesterol, phospholipid and/or triglyceride levels in the blood, and of hyperlipoproteinemia, involving an imbalance of the lipoproteins. The most serious condition associated with hyperlipidemia and hyperlipoproteinemia is atherosclerosis, a form of artheriosclerosis characterized by lipid accumulation and thickening of the walls of both medium-sized and large arteries such as the aorta. Their walls are thereby weakened and the elasticity and effective internal size of the arteries decreased. Atherosclerosis, the most common cause of coronary artery disease, is of great medical importance since it tends to occlude those arteries supplying blood to the heart muscles and brain, thereby producing permanent damage to these organs. Such damage may lead to ischemic heart disease, congestive heart failure, life-threatening arrhythmias, senility, or stroke. Involvement of leg arteries may lead to gangrene and loss of the limb. It has been known for more than 100 years that cholesterol is a major component of atherosclerotic lesions or plaques. Investigators have been trying to determine the role of cholesterol in their initiation and development and also, most importantly, whether lesion formation can be prevented or reversed and enlargement of lesions be slowed or stopped. The earliest lesions are now known to be fatty streaks, largely of cholesterol, which often progress in stages to plaques containing cellular, fibrous and calcified material in addition to the lipids.

The evidence that hyperlipidemia is one of the factors involved in coronary heart disease is very impressive. A most important study carried out in Framingham, Mass. (Gordon & Verter, 1969) in over 5,000 persons for more than 12 years established a correlation between high concentrations of blood cholesterol and increased risk of heart attack. Although the causes of coronary artery disease are multiple, one of the most constant factors has been the elevated concentration of lipids in the blood plasma. A combined elevation of cholesterol and triglycerides has been shown (Carlson & Bottiger, 1972) to carry the highest risk of coronary heart disease. The majority of patients with ischemic heart disease or peripheral vascular disease were found to have hyperlipoproteinemia, involving very low-density and/or low-density lipoproteins (Lewis et al. 1974).

The reason for most treatment of hyperlipidemia or hyperlipoproteinemia is for arresting, reversing or preventing atherosclerosis. In the past, attempts have been made to lower the levels of cholesterol, phospholipids, and triglycerides in the blood by the oral feeding of various substances which have been generally referred to in the art as hypolipidemic agents or hypocholesteremic adjuvants. Typical of such substances are lecithin, pectin, cottonseed oil, and the mucilaginous substances listed in the U.S. Pat. No. 3,148,114. In addition, several synthetic hypolipidemic agents are now available, namely, clofibrate, D-thyroxine, cholestyramine and nicotinic acid [(Levy & Frederickson, Postgraduate Medicine 47, 130 (1970)]. Clofibrate has the undesirable side-effect of causing hypertrophy of the liver in some patients.

The development of agents capable of reducing elevated blood lipids and of favorably altering blood-lipoprotein patterns is considered by medical authorities to be extremely important for the treatment and prevention of atherosclerosis. Orally active agents are required since patients usually take them for a number of years.

DETAILED DESCRIPTION OF THE INVENTION

The compounds of this invention are novel 2-substituted 4'-(monoalkylamino)acetophenones and have useful biological and pharmacological properties. No hypolipidemic activity has been reported in the literature for these compounds and they are different in structure from other hypolipidemic agents. The compounds of this invention lower serum-lipid concentrations and also minimize atheroma formation in the aorta. These compounds provide the oral administration required of hypolipidemic agents, which patients usually take for many years.

We have now found that the 2-substituted 4'-(monoalkylamino)acetophenones of the present invention can safely and effectively lower both serum sterols and triglycerides in warm-blooded mammals. Such actions on serum lipid components are considered to be very useful in the treatment of atherosclerosis, especially in contrast to available drugs whose action is much more limited. For some time it has been considered desirable to lower serum lipid levels and to correct lipoprotein imbalance in mammals as a preventive measure against atherosclerosis. The compounds of the present invention do not act by blocking late stages of cholesterol biosynthesis and thus do not produce accumulation of intermediates such as desmosterol, as equally undesirable as cholesterol itself. Compounds with the combination of therapeutically favorable characteristics possessed by those of the present invention can be safely administered to warm-blooded mammals for the treatment of hyperlipidemic and atherosclerotic states found in subjects with or prone to heart attacks, to peripheral or cerebral vascular disease, and to stroke.

The 2-substituted 4'-(monoalkylamino)acetophenones of the present invention are, in general, white crystalline solids having characteristic melting points and absorption spectra. They are soluble in organic solvents such as lower alkanols, chloroform, benzene, dimethylformamide, and the like but are generally not very soluble in water.

The 2-substituted 4'-(monoalkylamino)acetophenones of the present invention are organic bases and may be converted to their non-toxic acid-addition salts with a variety of pharmacologically acceptable organic and inorganic salt-forming reagents. Thus, acid-additon salts may be formed by admixture of the organic free base in a neutral solvent with one or two equivalents of an acid such as sulfuric, phosphoric, hydrochloric, hydrobromic, trifluoroacetic, citric, succinic, ascorbic, and the like. In addition, the enolic forms of the novel compounds of the present invention and those compounds wherein $R_2$ and/or $R_3$ contain acidic groups form pharmaceutically acceptable cationic salts with bases such as the alkali metal hydroxides, alkaline earth metal hydroxides, and the like.

The novel compounds of the present invention may be readily prepared by the following methods.

GENERAL METHOD

Certain of the 2-substituted 4'-(monoalkylamino)acetophenones (I) of this invention may be prepared by reaction of the benzoic acid derivative (II), wherein Y is $$\overset{H}{\underset{|}{R_1-N}} \text{ or a group}$$

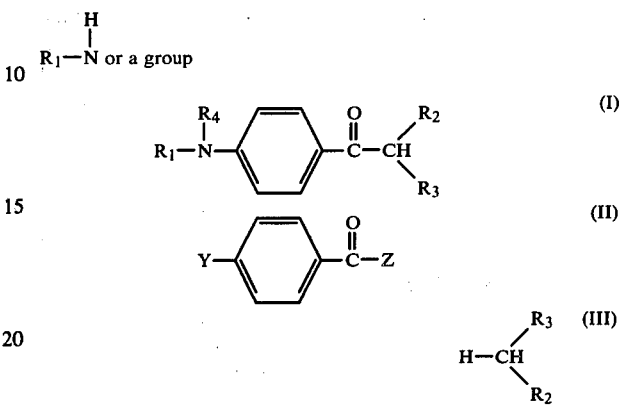

convertible thereinto such as N-t-butyloxycarbonyl-alkylamino, N-trifluoroacetyl-alkylamino, N-benzyloxycarbonyl-alkylamino, alkylammonio ($R_1-N^+H_2-$), nitro, or azido and wherein Z is a halide group, a mixed anhydride group such as acyloxy, alkyl or arylsulfonyloxy and the like, a normal ester such as methyl, an activated ester such as carboxy or carboalkoxymethyl, 4-nitrophenyl and the like, an N-oxide such as N-oxysuccinimide and the like, or an activated amide such as 1-imidazolyl and the like, with 2 moles of a reactive salt (e.g., sodium, triethylamine) or metal chelate (e.g., calcium, copper, etc.) or with a reactive derivative (e.g., halo or the like, $X-CHR_2R_3$) of the methylene compound (III) in which case Z is a negative charge on the carbon atom whose carbonyl group is in a protected form as a cyanoamino derivative, dimethylhydrazone or the like. An alternative preparation of I is the reaction

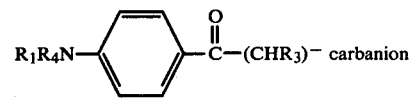

with $Z-R_2$. In most cases, the sodium or organic base salt of III is the reactive form used in the reaction. $R_1$, $R_2$, and $R_3$ are as previously defined except where the group itself would interfere with the reaction (e.g., carboxy). In some cases, the final step in the preparation of the 2-substituted 4'-(alkylamino)acetophenones is removal of an

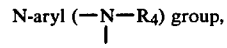

especially N-acyl protecting groups. Such N-acyl compounds arise as described above or via Friedel-Crafts acylation of aniline derivative (IV) with the disubstituted acetyl chloride (V) and the like.

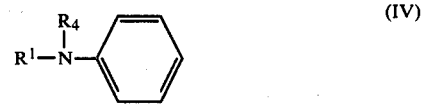

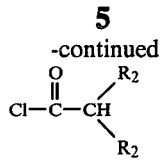

The benzoic acid derivative (II) is in general added to the preformed sodium salt of the methylene compound (III) to give the desired product. However, the sodium salt is sometimes prepared in the presence of (II), as are customarily the enolate salts of triethylamine, pyridine and the like. The preparation of the sodium salt can be accomplished by reaction of sodium hydride or other suitable bases with the methylene compound (III) in an appropriate solvent such as 1,2-dimethoxyethane, tetrahydrofuran, etc. Reaction of the sodium salt with the benzoic acid derivative is carried out at temperatures of 0°–110° C. A typical example of this general method is reaction of the sodium salt of diethylmalonate with p-(hexadecylamino)benzoyl chloride to give diethyl acid p-(hexadecylamino)benzoylmalonate. It should be noted that this type of reaction includes compounds wherein $R_3$ is hydrogen such as the case where (III) is dimethylsulfone. Pharmacologically acceptable acid-addition salts of the products may be formed by treating the 4-(monoalkylamino)acetophenones with appropriate acids, such as hydrochloric acid, etc. In addition, pharmacologically acceptable enolate and carboxylate salts of these compounds may be obtained by treatment with a suitable base.

It should be noted that certain of these keto compounds exist as mixtures with one or more enol forms, often with one form predominating. Such is the case of ethyl 2-cyano-2-p-(hexadecylamino)benzoylacetate, which exists predominantly in the enol form:

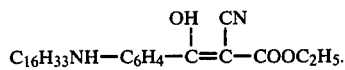

In other cases such as when $R_2$ and/or $R_3$ are aroyl, the two or three possible enol forms will all be present.

An alternative procedure for preparing these 2-substituted 4'-(monoalkylamino)acetophenones consists of alkylating a substituted 4-aminoacetophenone with an agent RX such as an alkyl halide, sulfate, mesylate, tosylate, trifluoromethanesulfonate and the like at 50°–140° C.

An example of this type of reaction is the alkylation of p-aminobenzoylacetonitrile with hexadecyl bromide to yield p-(hexadecylamino)benzoylacetonitrile, as in Example 1.

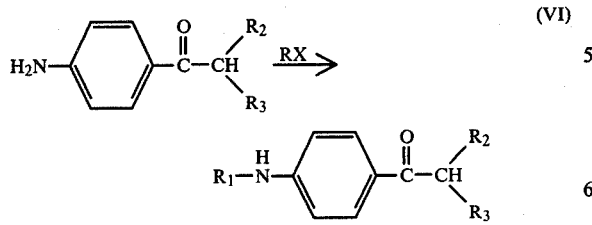

The above procedure is also used to prepare the 2-substituted 4'-(monoalkylamino)acetopheones where $R_3$ is hydrogen and $R_2$ is alkoxycarbonylmethyl. For example, alkylation of methyl 3-(p-aminobenzoyl)propionate with hexadecyl bromide yields methyl 3-p-[hexadecylamino]benzoylpropionate. Hydrolysis of the ester with potassium hydroxide yields 3-p-[hexadecylamino]benzoylpropionic acid (VII).

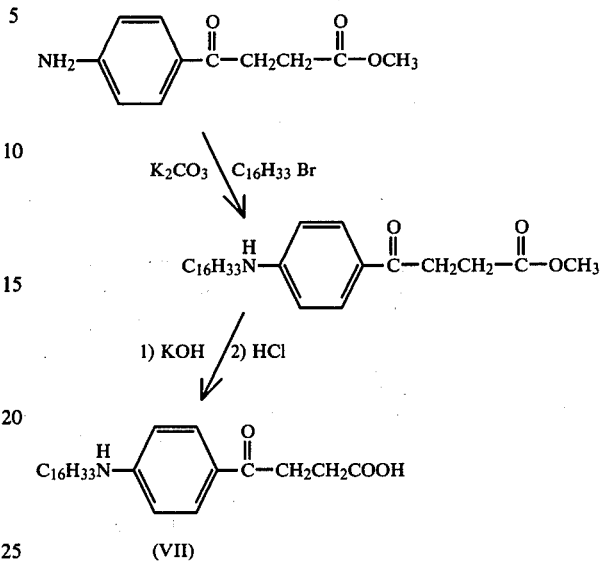

The related carboxylic acids where $R_3$ is hydrogen and $R_2$ is carboxyethyl or ester or a longer chain carboxylalkyl group can be prepared by aroylation of an appropriate carbanion as previously described. Reaction of the acid chloride (VIII) with the sodium α-carbanion of a dicarboxylic acid ester (IX) yields a compound (X) which can be hydrolyzed to the diacid and concurrently monodecarboxylated to the desired acid (XI). Simple esterification of the acid yields the ester (XII). For example,

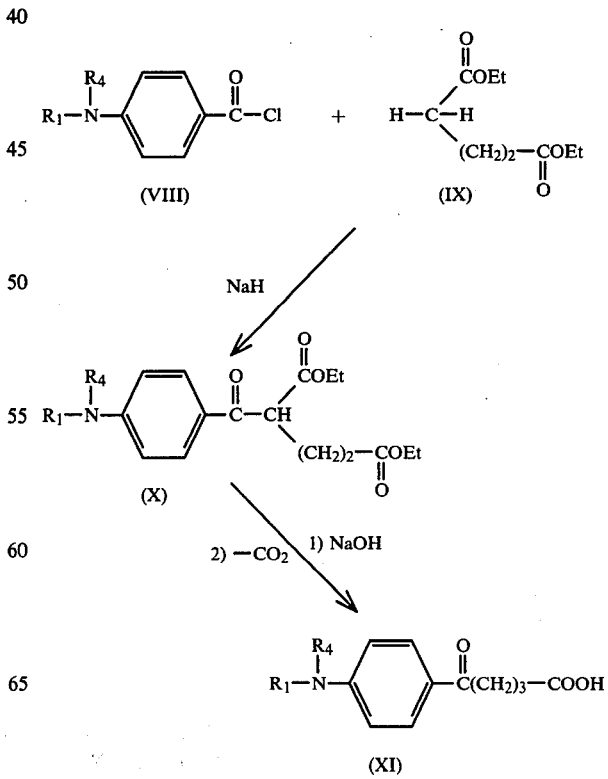

-continued

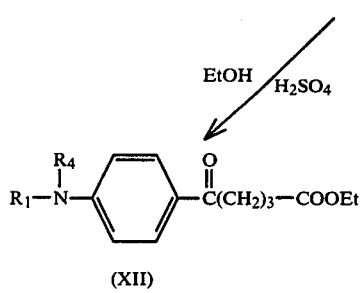

(XII)

In the case of a p-(alkylamino)benzoylacetic acid, wherein $R_2$ is carboxy and $R_3$ is hydrogen in (I), a modified procedure is employed. Reaction of the appropriate acid chloride (VIII) with the sodium salt of t-butyl ethyl malonate (XIII) as described above gives the substituted malonate (XIV). The t-butyl group is then selectively removed with acid and this is accompanied by decarboxylation to give the ethyl p-(alkylamino)benzoylacetate (XV). The acid (XVI) is obtained by careful hydrolysis of the ester or by use of the di-t-butyl ester.

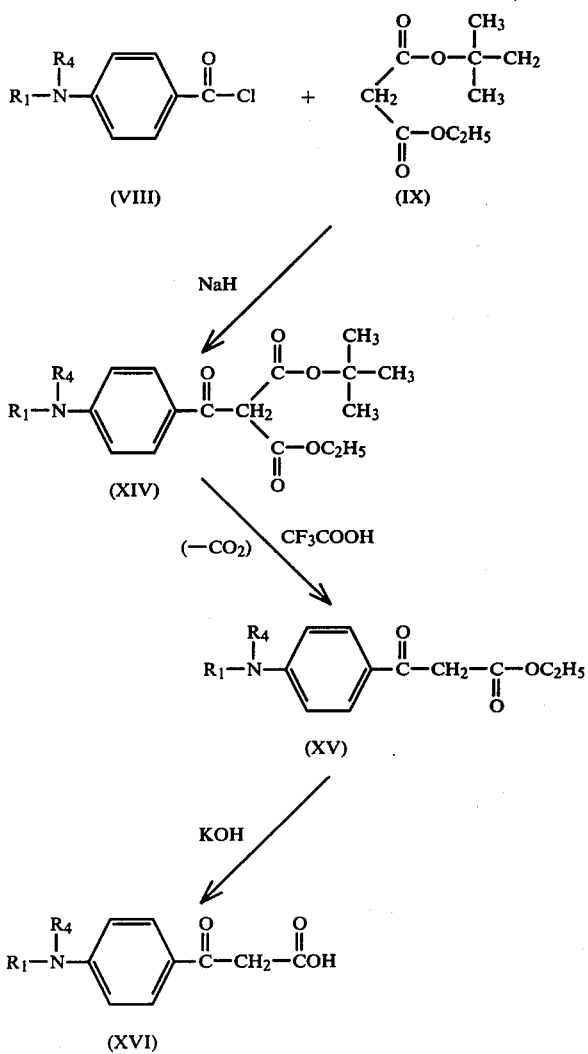

Another variation of the general acylation method is the reaction at 10°–110° C. of a normal ester (XVII) or an activated ester with a suitable methylene compound (III) carbanion such as XVIII.

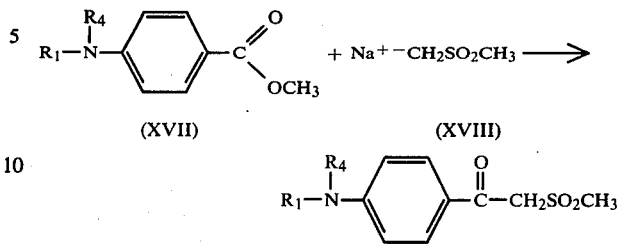

Certain derivatives

or the aminophenyl nitrogen atom are useful for providing greater solubility, more uniform and reliable intestinal absorption, and for a certain degree of modification of the pharmacology of the compounds of the present invention. Some of these derivatives can be converted to the corresponding N-H forms by the acidity of the stomach or the alkalinity of the small intestine. Others are converted by metabolic processes. The methyl and carboxymethyl derivatives and the like are prepared by the alkylation and acylation methods above. Derivatives such as the acetyl and succinyl compounds may be prepared using acetic anhydride or succinic anhydride in acetic acid and other organic solvents at temperatures moderate enough to avoid acylation of the enol moiety.

The novel compounds of the present invention are not only potent hypolipidemic agents but also prevent or diminish the formation or enlargement of arterial plaques in mammals when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 gram to about 7.0 grams of the active compound for a subject of about 70 kg. of body weight are administered in a 24-hour period. This dosage regimen may be adjusted to provide the optimum therapeutic response. For example, several divided doses may be administered daily or the dose may be proportionally reduced as indicated by the exigencies of the therapeutic situation. A decided practical advantages of this invention is that the active compound may be administered conveniently by the oral route. It is not known how these novel compounds operate in the blood serum and no theory of why these compounds so operate is advanced. It is not intended that the present invention should be limited to any particular mechanism of action of lowering serum lipids or of meliorting atherosclerosis, or be limited to compounds acting by only one mechanism.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, trouches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active ingredient in such thereapeutically useful compositions is such that a suitable dosage will be obtained,. Preferred compositions according to the present invention are prepared so that an oral dosage unit form contains between about 50 and 250 mg. of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added, or a flavoring agent such as peppermint, oil of wintergreen, or cherry flavoring. When the dosage unit form is a capsule, it may contain in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active ingredients may be incorporated into sustained-release preparations and formulations.

The invention will be described in greater detail in conjunction with the following specific examples.

EXAMPLE 1 p-(Hexadecylamino)benzoylacetonitrile

A solution of 3.2 g. of p-aminobenzoylacetonitrile in 25 ml. of dry hexamethylphosphoramide containing 3.0 g. of hexadecyl bromide is heated at 100° C. under $N_2$ for 11 hours. The solution is cooled, diluted with water and filtered. The solid thus obtained is recrystallized from methylene chloride-hexane. This material is chromatographed on silica gel and then recrystallized from acetic acid to yield pure product.

By employing an equimolar amount of decyl bromide, octyl bromide, dodecyl bromide, octadecyl bromide, 1-methylpentadecyl bromide, 15-methylhexadecyl bromide or 13,13-dimethyltetradecyl bromide instead of the hexadecyl bromide above, there is obtained p-(decylamino)benzoylacetonitrile, p-(octylamino)benzoylacetonitrile, p-(dodecylamino)benzoylacetonitrile, p-(octadecylamino)benzoylacetonitrile, p-[(1-methylpentadecyl)amino]benzoylacetonitrile, p-[(15-methylhexadecyl)amino]benzoylacetonitrile, p-[(13,13-dimethyltetradecyl)amino]benzoylacetonitrile, respectively.

EXAMPLE 2 p-(Hexadecylamino)benzoyl chloride hydrochloride

A solution of 25 g. of p-(hexadecylamino)benzoic acid, 830 ml. of methylene chloride, 130 ml. of 1,2-dimethoxyethane and 28 ml. of thionyl chloride is refluxed for 1.5 hours. The resulting orange solution is cooled, and then concentrated. Toluene is then added and the solution concentrated to remove the excess thionyl chloride affording an amber oil of p-hexadecylaminobenzoyl chloride hydrochloride.

By employing an equimolar amount of p-(octylamino)benzoic acid, p-(nonylamino)benzoic acid, p-(decylamino)benzoic acid, p-(undecylamino)benzoic acid, p-(dodecylamino)benzoic acid, p-(tridecylamino)benzoic acid, p-(tetradecylamino)benzoic acid, p-(pentadecylamino)benzoic acid, p-(heptadecylamino)benzoic acid, p-(octadecylamino)benzoic acid, p-(nonadecylamino)benzoic acid, p-[(1-methylpentadecyl)amino]benzoic acid, p-[(15-methylhexadecyl)amino]benzoic acid, and p-[13,13-dimethyltetradecyl)amino]benzoic acid instead of the p-(hexadecylamino)benzoic acid above, there is obtained p-(octylamino)benzoyl chloride hydrochloride, p-(nonylamino)benzoyl chloride hydrochloride, p-(decylamino)benzoyl chloride hydrochloride, p-(undecylamino)benzoyl chloride hydrochloride, p-(dodecylamino)nenzoyl chloride hydrochloride, p-(tridecylamino)benzoyl chloride hydrochloride, p-(tetradecylamino)benzoyl chloride hydrochloride, p-(pentadecylamino)benzoyl chloride hydrochloride, p-(heptadecylamino)benzoyl chloride hydrochloride, p-(octadecylamino)benzoyl chloride hydrochloride p-(nonadecylamino)benzoyl chloride hydrochloride, p-[(1-methylpentadecyl)amino]benzoyl chloride hydrochloride, p-[(15-methylhexadecyl)amino]benzoyl chloride hydrochloride, and p-[(13,13-dimethyltetradecyl)amino]benzoyl chloride, respectively.

EXAMPLE 3

N-Trifluoroacetyl-p-(hexadecylamino)benzoyl chloride

To a stirred, ice-cold suspension of 9.0 g. of p-hexadecylaminobenzoic acid in 100 ml. of dimethoxyethane and 16 ml. of pyridine is added 18 ml. of trifluoroacetic anhydride. The solution is stirred at 0° C. for 30 minutes, then 30 minutes at room temperature. The solution is diluted with 300 ml. of ether and 100 g. of ice. After stirring vigorously for 15 minutes, the phases are separated, the ether solution is washed with brine, dried and evaporated to a white, amorphous solid.

To 9.2 g. of the above product in 30 ml. of methylene chloride and 0.5 ml. of dimethylformamide is added 5.7 ml. of thionyl chloride. After 20 hours at reflux, the solvent is evaporated to yield a light yellow, mobile oil.

By employing an equimolar amount of p-(octylamino)benzoic acid, p-(decylamino)benzoic acid, p-(pentadecylamino)benzoic acid, p-(octadecylamino)benzoic acid, p-[(1-methylpentadecyl)amino]benzoic acid, p-[(15-methylhexadecyl)amino]benzoic acid and p-[(13,13-dimethyltetradecyl)amino]benzoic acid instead of the p-(hexadecylamino)benzoic acid above, there is obtained N-trifluoroacetyl-p-(octylamino)benzoyl chloride, N-trifluoroacetyl-p-(decylamino)benzoyl chloride, N-trifluoroacetyl-p-(pentadecylamino)benzoyl chloride, N-trifluoroacetyl-p-(octadecylamino)benzoyl chloride, N-trifluoroacetyl-p-[(1-methylpentadecyl)amino]benzoyl chloride, N-trifluoroacetyl-p-[(15-methylhexadecyl)amino]benzoyl chloride and N-trifluoroacetyl-p-[(13,13-dimethyltetradecyl)amino]benzoyl chloride, respectively.

EXAMPLE 4

Diethyl p-(hexadecylamino)benzoylmalonate

A solution of 26.6 g. of diethyl malonate and 10 ml. of 1,2-dimethoxyethane (DME) is added to a suspension of 4.0 g. of sodium hydride in DME under argon. A solution of 17.3 g. of p-(hexadecylamino)benzoyl chloride hydrochloride in DME is then added. The reaction mixture is refluxed for 4.5 hours, cooled, poured on ice, acidified, and extracted with ether. The ether solution is washed with water, saturated sodium chloride solution, dried over anhydrous sodium sulfate and concentrated to dryness. Addition of a small amount of ethanol to the residue gives a solid which is filtered and discarded. The ethanol filtrate is concentrated and the residue is recrystallized from diethyl ether.

By employing an equimolar amount of p-(octylamino)benzoyl chloride hydrochloride, p-(tridecylamino)benzoyl chloride hydrochloride, p-(pentadecylamino)benzoyl chloride hydrochloride, p-(nonadecylamino)benzoyl chloride hydrochloride, p-[(1-methylpentadecyl)amino]benzoyl chloride hydrochloride, and p-[(15-methylhexadecyl)amino]benzoyl chloride hydrochloride instead of the p-hexadecylaminobenzoyl chloride hydrochloride above, there is obtained the diethyl p-(octylamino)benzoyl-p-(tridecylamino)benzoyl-, p-(pentadecylamino)benzoyl-, p-nonadecylamino)benzoyl-, p-[(1-methylpentadecyl)amino]benzoyl-, and p-[(15-methylhexadecyl)amino]benzoyl- malonate esters, respectively.

EXAMPLE 5 t-Butyl ethyl p-(hexadecylamino(benzoylmalonate

A solution of 28.0 g. of t-butyl ethyl malonate and 10 ml. of 1,2-dimethoxyethane (DME) is added to a suspension of 4.0 g. of sodium hydride in DME under argon. A solution of 17.3 g. of p-(hexadecylamino)benzoyl chloride hydrochloride in DME is then added. The reaction mixture is refluxed for 5 hours, cooled, poured on ice and extracted with ether. The ether solution is washed with water, saturated sodium chloride solution, dried over anhydrous sodium sulfate and concentrated to dryness. The residue is then recrystallized from ether. A second recrystallization is carried out from methylene chloride to give the product.

By employing an equimolar amount of p-(octylamino)-benzoyl chloride hydrochloride, p-(dodecylamino)benzoyl chloride hydrochloride, p-(pentadecylamino)benzoyl chloride hydrochloride, p-(octadecylamino)benzoyl chloride hydrochloride, p-[(1methylpentadecyl)amino]benzoyl chloride hydrochloride and p-[(15-methylhexadecyl)amino]benzoyl chloride hydrochloride instead of the p-(hexadecylamino)benzoyl chloride hydrochloride above, there is obtained the t-butyl ethyl p-(octylamino)benzoyl-, p-(dodecylamino)benzoyl-, p-(pentadecylamino)benzoyl-, p-(octadecylamino)benzoyl-, p-[(1-methylpentadecyl)-amino]benzoyl-, and p-[(15-methylhexadecyl)amino]benzoyl-, malonate esters, respectively.

EXAMPLE 6

2Cyano-2-p-(hexadecylamino)benzoylacetate

A solution of 18.8 g. of ethyl cyanoacetate and 10 ml. of 1,2-dimethoxyethane (DME) is added to a suspension of 4.0 g. of sodium hydride in DME under argon. A solution of 17.3 g. of p-(hexadecylamino)benzoyl chloride hydrochloride in DME is then added. The reaction mixture is refluxed for 5 hours, cooled, poured on ice and acidified with hydrochloric acid to pH 3. The resulting solid is filtered, washed three times with water and dried. Recrystallization from hexane yields the product.

By employing an equimolar amount of p-(octylamino)-benzoyl chloride hydrochloride, p-(dodecylamino)benzoyl chloride hydrochloride, p-(pentadecylamino)benzoyl chloride hydrochloride, p-(octadecylamino)benzoyl chloride hydrochloride, p-[(1-methylpentadecyl)amino]benzoyl chloride hydrochloride and p-[(15-methylhexadecyl)amino]benzoyl chloride hydrochloride instead of the p-(hexadecylamino)benzoyl chloride hydrochloride above, there is obtained the ethyl 2-cyano-2-(p-octylaminoenzoyl)-, 2-cyano-2-(p-dodecylaminobenzoyl)-, 2-cyano-2-(p-pentadecylaminobenzoyl)-, 2-cyano-2-(p-octadecylaminobenzoyl)-, 2-cyano-2-[p-[(1-methylpentadecyl)amino]-benzoyl]-, and 2-cyano-2-[p-[(15-methylhexadecyl)amino]-benzoyl]-acetate esters, respectively.

EXAMPLE 7

Ethyl 2-p-hexadecylaminobenzoylacetoacetate

A solution of 21.6 g. of ethyl acetoacetate and 10 ml. of 1,2-dimethoxyethane (DME) is added to a suspension of 4.0 g. of sodium hydride in DME under argon. A solution of 17.3 g. of p-(hexadecylamino)benzoyl chloride hydrochloride in DME is then added. The reaction mixture is refluxed for 5 hours, cooled, poured on ice and extracted with ether. The ether solution is washed with water, saturated sodium chloride solution, dried over anhydrous sodium sulfate and concentrated to dryness. The subject product is isolated by column chromatography,.

By employing an equimolar amount of p-(octylamino)-benzoyl chloride hydrochloride, p-(tridecylamino)benzoyl chloride hydrochloride, p-(pentadecylamino)benzoyl chloride hydrochloride, p-(nonadecylamino)benzoyl chloride hydrochloride, p-[(1-methylpentadecyl)amino]benzoyl chloride hydrochloride, p-[(15-methylhexadecyl)amino]benzoyl chloride hydrochloride and p-[(13,13-dimethyltetradecyl]amino]benzoyl chloride hydrochloride instead of the p-(hexadecylamino)benzoyl chloride hydrochloride above, there is obtained the ethyl 2-p-(octylamino)benzoyl-, 2-p-(tridecylamino)benzoyl-, 2-p-(pentadecylamino)benzoyl-, 2-p-(nonadecylamino)benzoyl-, 2-p-[(1-methylpentadecyl)amino]benzoyl-, 2-p-[(15-methylhexadecyl)amino]benzoyl-, and 2-p-[(13,13-dimethyltetradecyl)-amino]benzoyl- acetoacetate esters respectively.

EXAMPLE 8 p-(Hexadecylamino)benzoylacetic Acid

Two grams of ethyl p-(hexadecylamino)benzoylacetate is added to a solution of potassium hydroxide in water-ethanol. Reaction mixture is stirred for 24 hours at room temperature. Careful neutralization with sulfuric acid gave a precipitate which was filtered, washed with water, and dried to give the product.

By employing an equimolar amount of ethyl p-(octylamino)benzoylacetate, ethyl p-(dodecylamino)benzoylacetate, ethyl p-(tetradecylamino)benzoylacetate, and ethyl p-(nonadecylamino)benzoyl acetate instead of the ethyl p-hexadecylaminobenzoyl acetate above, there is obtained p-octylaminobenzoylacetic acid, p-dodecylaminobenzoylacetic acid, p-tetradecylaminobenzoylacetic acid, and p-nonadecylaminoenzoylacetic acid, respectively.

EXAMPLE 9

4'-Hexadecylamino-2-(methylsulfonyl)acetophenone

A solution of 864 mg. (0.036 moles) of sodium hydride, 3.2 g. (0.034 moles) of dimethylsulfone, 4 ml. of dimethylsulfoxide and 20 ml. of 1,2-dimethoxyethane is stirred at 60° C. for one hour under an atmosphere of argon. To this is then added a solution of 5.0 g. (0.013 moles) of methyl p-(hexadecylamino)benzoate and 50 ml. of tetrahydrofuran and the reaction is stirred at 60° C. for an additional 1.5 hours. The reaction mixture is cooled, poured onto ice, acidified with dilute hydrochloric acid to pH 3 and then extracted with chloroform. The organic layer is washed three times with water, saturated sodium chloride solution, dried over anhydrous sodium sulfate and then concentrated to dryness. The crude solid is chromatographed on silica gel eluting with methylene chloride to give the product.

By employing an equimolar amount of methyl p-(dodecylamino)benzoate, methyl p-(pentadecylamino)benzoate, methyl p-[(1-methylpentadecyl)amino]benzoate, and methyl p-[(15-methylhexadecyl)amino]benzoate instead of the methyl p-(hexadecylamino)benzoate above, there is obtained the 4'-dodecylamino-2-(methylsulfonyl)-, 4'-pentadecylamino-2-(methylsulfonyl)-, 4'-(1-methylpentadecyl)amino-2-(methylsulfonyl)-, and 4'-(15-methylhexadecyl)amino-2-(methylsulfonyl)-acetophenones, respectively.

EXAMPLE 10

4'-Hexadecylamino-2-(methylsulfinyl)acetophenone

To a solution of 5.8 g. of dimethyl sulfoxide, dried over sieves, and 50 ml. of tetrahydrofuran (THF) is slowly added 28 ml. (0.07 moles) of n-butyl lithium (2.42M in hexane). To this mixture is added 10 g. of methyl p-(hexadecylamino)benzoate in 200 ml. of THF. After two hours, the reaction mixture is poured onto ice, acidified with diluted hydrochloric acid and quickly extracted with chloroform. The chloroform layer is washed with water, saturated sodium chloride solution, and dried over anhydrous sodium sulfate. Concentration affords a solid which is washed with 500 ml. of hot hexane, filtered hot and then washed with a second 50 ml. portion of hexane. The white solid is dried in vacuo yielding the product.

By employing an equimolar amount of methyl p-(dodecylamino)benzoate, methyl p-(pentadecylamino)benzoate, methyl p-[(1-methylpentadecyl)amino]benzoate, and methyl p-[(15-methylhexadecyl)amino]benzoate instead of the methyl p-(hexadecylamino)benzoate above, there is obtained the 4'-dodecylamino-2-(methylsulfinyl)-, 4'-pentadecylamino-2-(methylsulfinyl)- 4'-(1-methylpentadecyl)amino-2-(methylsulfinyl)-, and 4'-(15-methylhexadecyl)amino-2-(methylsulfinyl-acetophenones, respectively.

EXAMPLE 11

4'-Hexadecylamino-2-(phenylsulfonyl)acetophenone

A solution of 864 mg. (0.036 moles) of sodium hydride, 5.3 g. (0.034 moles) of methylphenylsulfone, 4 ml. of dimethyl sulfoxide and 20 ml. of 1,2-dimethoxyethane is stirred at 60° C. for one hour under an atmosphere of argon. To this is then added a solution of 5.0 g. (0.013 moles) of methyl p-(hexadecylamino)benzoate and 50 ml. of tetrahydrofuran and the reaction is stirred at 60° C. for an additional 1.5 hours. The reaction mixture is cooled, poured onto ice, acidified with dilute hydrochloric acid to pH 3 and then extracted with chloroform. The organic layer is washed three times with water, saturated sodium chloride solution, dried over anhydrous sodium sulfate and then concentrated to dryness. The crude solid is chromatographed on silica gel eluting with methylene chloride to give the product.

By employing an equimolar amount of methyl p-(decylamino)benzoate, methyl p-(nonadecylamino)benzoate, methyl p-[(1-methylpentadecyl)amino]benzoate, and methyl p-[(15-methylhexadecyl) amino]benzoate instead of the methyl p-(hexadecylamino)benzoate above, there is obtained the 4'-decylamino-2-(phenylsulfonyl)-, 4'-nonadecylamino-2-(phenylsulfonyl)-, 4'-(11-methylpentadecyl)amino-2-(phenylsulfonyl)-, and 4'-(15-methylhexadecyl)amino-2-(phenylsulfonyl)-acetophenones, respectively.

EXAMPLE 12

4'-Hexadecylamino-2-(phenylsulfinyl)acetophenone

To a solution of 6.2 g. of methylphenylsulfoxide, dried over sieves, and 50 ml. of tetrahydrofuran (THF) is slowly added 28 ml. (0.07 moles) of n-butyl lithium (2.42M in hexane). To this mixture was added 10 g. of methyl p-(hexadecylamino)benzoate in 200 ml. of THF. After two hours, the reaction mixture is poured into ice, acidified with diluted hydrochloric acid and quickly extracted with chloroform. The chloroform layer is washed with water, saturated sodium chloride solution and dried over anhydrous sodium sulfate. Concentration afforded a solid which is washed with 500 ml. of hot hexane, filtered hot, and then washed with a second 50 ml. portion of hexane. The white solid is dried in vacuo yielding the product.

By employing an equimolar amount of methyl p-(decylamino) benzoate, methyl p-(nonadecylamino)benzoate, methyl p-[(1-methylpentadecyl)amino]benzoate, and methyl p-[(15-methylhexadecyl)amino]benzoate instead of the methyl p-(hexadecylamino)benzoate above, there is obtained the 4'-decylamino-2-(phenylsulfinyl), 4'-nonadecylamino-2-(phenylsulfinyl)-, 4'-(1-methylpentadecyl)amino-2-(phenylsulfinyl)-, and 4'-(15-methylhexadecyl)amino-2-(phenylsulfinyl)-acetophenones, respectively.

EXAMPLE 13

3-p-(Hexadecylamino)benzoyl-2,4-pentanedione

A solution of 28.4 g. of 2,4-pentaedione and 20 ml. of 1,2-dimethyoxyethane (DME) is added to a suspension of 13.6 g. of sodium hydride in 220 ml. of DME under argon. A solution of 28.7 g. of p-(hexadecylamino)benzoyl chloride hydrochloride in DME is then added. The reaction mixture is stirred at room temperature for 12 hours, cooled, poured on ice and extracted with ether. The ether solution is washed with water, saturated sodium chloride solution, dried over anhydrous sodium sulfate and concentrated. The residue is then chromatographed over silica gel to yield the product. Recrystallization from methylene chloride gives the product.

By employing an equimolar amount of p-(octylamino)benzoyl chloride hydrochloride, p-(tridecylamino)benzoyl chloride hydrochloride, p-(pentadecylamino)benzoyl chloride hydrochloride, p-(nonadecylamino)benzoyl chloride hydrochloride, p-[(1-methylpentadecyl)amino]benzoyl chloride hydrochloride and p-[(15-methylhexadecyl)amino]benzoyl chloride hydrochloride instead of the p-(hexadecylamino)benzoyl chloride hydrochloride above, there is obtained the 3-p-(octylamino)benzoyl-, 3-p-(tridecylamino) benzoyl-, 3-p-(pentadecylamino)benzoyl-, 3-p-(nonadecylamino)benzoyl-, p-[(1-methylpentadecyl)amino]-benzoyl-, and 3-p-[(15-methylhexadecyl)amino]benzoyl-2,4-pentanediones, respectively.

EXAMPLE 14

Ethyl 2-benzoyl-2-(p-hexadecylaminobenzoyl)acetate

A solution of 31.8 g. of ethyl benzoyolacetate and 10 ml. of 1,2-dimethoxyethane (DME) is added to a suspension of 4.0 g. of sodium hydride in DME under argon. A solution of 17.3 g. of p-(hexadecylamino)benzoyl chloride hydrochloride in DME is then added. The reaction mixture is refluxed for 5 hours, cooled, poured on ice and extracted with ether. The ether solution is washed with water, saturated sodium chloride solution, dried over anhydrous sodium sulfate and concentrated to dryness. The product is isolated by column chromatography.

By employing an equimolar amount of p-(octylamino)benzoyl chloride hydrochloride, p-(dodecylamino)benzoyl chloride hydrochloride, p-(pentadecylamino)benzoyl chloride hydrochloride, p-(octadecylamino)benzoyl chloride hydrochloride, p-[(1-methylpentadecyl)amino]benzoyl chloride hydrochloride and p-[(15-methylhexadecyl)amino]benzoyl chloride hydrochloride instead of the p-hexadecylaminobenzoyl chloride hydrochloride avoe, there is obtained the ethyl 2-benzoyl-2-(p-octylaminobenzoyl)-, 2-benzoyl-2-(p-dodecylaminobenzoyl)-, 2-benzoyl-2-(p-pendadecylaminobenzoyl)-, 2-benzoyl-2-(p-octadecylaminobenzoyl)-, 2-benzoyl-2-[p-[(1-methylpentadecyl)amino]benzoyl]-, and 2-benzoyl-2-[p-[(15-methylhexadecyl)amino]benzoyl]- acetate esters, respectively.

EXAMPLE 15

3-p-(Hexadecylamino)benzoylpropionic Acid

A solution of 5.4 g. of methyl 3-p-(hexadecylamino)benzoylpropionate is stirred with 5.4 g. of potassium hydroxide in 100 ml. of 95% ethanol for 3 hours at reflux. The reaction mixture is cooled, diluted with 50 ml. of ethanol and 100 ml. of water, and neutralized with hydrochloric acid. The solution is cooled to room temperature and filtered. The white solid is washed with 50% aqueous ethanol and dried. The product is recrystallized from ethanol.

By employing an equimolar amount of methyl 3-p-(octylamino)benzoylpropionate, methyl 3-p-(dodecylamino)benzoylpropionate, methyl 3-p-(pentadecylamino)benzoylpropionate, methyl 3-p-(octadecylamino)benzoylpropionate, methyl 3-p-[(1-methylpentadecyl)amino]benzoylpropionate, and methyl 3-p-[(15-methylhexadecyl)amino]benzoylpropionate instead of the methyl 3-p-hexadecylaminobenzoylpropionate above, there is obtained the 3-p-(octylamino)benzoyl-, 3p-(dodecylamino)benzoyl-, 3-p-(pentadecylamino)benzoyl-, 3-p-(octadecylamino)benzoyl-, 3-p-[(1-methylpentadecyl)amino]benzoyl-, and 3-p-[(15-methylhexadecyl)amino]benzoyl- propionic acids, respectively.

EXAMPLE 16

4-p-(Hexadecylamino)benzoylbutyric Acid

To 2.0 g. of diethyl 2-p-[hexadecylamino]benzoylglutarate is added an excess of 1N sodium hydroxide. The reaction mixture is heated for 3 hours. After cooling, the mixture is acidified with diluted hydrochloric acid and then heated for an additional 30 minutes. After cooling, the mixture is extracted with ether and the ether solution is washed with water and dried. Concentration of the ether solution, followed by recrystallization of the residue from methylene chloride, gives the product.

By employing an equimolar amount of diethyl 2-p-(octylamino)benzoylglutarate, diethyl 2-p-(dodecylamino)benzoylglutarate, diethyl 2-p-(pentadecylamino)benzoylglutarate, diethyl 2-p(nonadecylamino)benzoylglutarate, diethyl 2-p-[(1-methylpentadecyl)amino]benzoylglutarate and diethyl 2-p-[(15-methylhexadecyl)amino]benzoylglutarate instead of the diethyl 2-p-(hexadecylamino)benzoylglutarate of the preceding paragraph, there is obtained the 4-p-(octylamino)benzoyl-, 4-p-(dodecylamino)benzoyl-, 4-p-(pentadecylamino)benzoyl-, 4-p-(nonadecylamino)benzoyl-, 4-p-[(1-methylpentadecyl)amino]benzoyl-, and 4-p-[(15-methylhexadecyl)amino]benzoyl- butyric acids, respectively.

EXAMPLE 17

Methyl 3-p-(hexadecylamino)benzoylpropionate

A mixture of 62 g. of methyl 3-(p-aminobenzoyl)propionate, 9.2 g. of hexadecyl bromide, and 4.2 g. of potassium carbonate is stirred for 20 hours at 125° C. under nitrogen. The mixture is then cooled to 25° C. and 30 ml. of water is added. After stirring, the product is filtered and washed with water. Recrystallization from methanol gives the product.

By employing an equimolar amount of octyl bromide, dodecyl bromide, pentadecyl bromide, octadecyl bromide, 1-methylpentadecyl bromide and 15-methylhexadecyl bromide instead of the hexadecyl bromide above, there is obtained the methyl 3-(p-octylaminobenzoyl)-, 3-(p-dodecylaminobenzoyl)3-(p-pentadecylaminobenzoyl)-, 3-(p-octadecylaminobenzoyl, 3-(p-[(1-methylpentadecyl)amino]benzoyl], and 3-[p-[(15-methylhexadecyl)amino]benzoyl]- propionate esters, respectively.

EXAMPLE 18

Methyl 3-p-aminobenzoylpropionate

A mixture of 35 g. of 3-p-acetamidobenzoylpropionic acid, 700 ml. of methanol and 1.4 ml. of concentrated sulfuric acid is refluxed for 76 hours. The solution is cooled to 35° C. and poured onto 7 g. of anhydrous sodium acetate while stirring. The reaction mixture is stirred in an ice-bath. The product is filtered and washed with cold methanol.

EXAMPLE 19

Ethyl p-(hexadecylamino)benzoylacetate

A solution of 3.0 g. of t-butyl ethyl p-(hexadecylamino)benzoylmalonate in 10 ml. of trifluoroacetic acid is warmed with stirring for 3 hours. The solution is poured onto ice and neutralized with potassium hydroxide. The resulting precipitate is washed with water and dried. Recrystallization from chloroform gives the desired product.

By employing an equimolar amount of t-butyl ethyl (p-octylaminobenzoyl)malonate, t-butyl ethyl (p-dodecylaminobenzoyl)malonate, t-butyl ethyl (p-pentadecylaminobenzoyl)malonate, t-butyl ethyl (p- octadecylaminobenzoyl)malonate, t-butyl ethyl [p-[(1-methylpentadecyl)amino]benzoyl]malonate and t-butyl ethyl [p-[(15-methylhexadecyl)amino]benzoyl]malonate instead of the t-butyl ethyl (p-hexadecylaminobenzoyl)malonate above, there is obtained the ethyl p-(octylamino)benzoyl-, p-(dodecylamino)benzoyl-, p-(pentadecylamino)benzoyl-, p-(octadecylamino)benzoyl-, p-[(1-methylpentadecyl)amino]-benzoyl-, and p-[(15-methylhexadecyl)amino]benzoyl- acetate esters, respectively.

EXAMPLE 20

Ethyl 4-p(hexadecylamino)benzoylbutyrate

To a solution of 50 ml. of ethanol and 2 ml. of sulfurnic acid is added 4.0 g. of 4-p-(hexadecylamino)benzoylbutyric acid. The mixture is refluxed for 6 hours and let cool. The reaction mixture is neutralized with sodium carbonate and the ethanol removed on the rotating evaporator. Recrystallization of the residue from hexane-chloroform gives the desired product.

By employing an equimolar amount of 4-(p-ocytlaminobenzoyl)butyric acid, 4-(p-dodecylaminobenzoyl)butyric acid, 4-(p-pentadecylaminobenzoyl)butyric acid, 4-(p-nonadecylaminobenzoyl)butyric acid, 4-[p-] (1-methylpentadecyl)amino[benzoyl]butyric acid and 4-[p-[(15-methylhexadecyl) amino]butyric acid instead of the 4-(p-hexadecylaminobenzoyl)butyric acid above, there is obtained the ethyl 4-(p-octylaminobenzoyl)4-(p-dodecylaminobenzoyl)-, 4-(p-pentadecylaminobenzoyl)-, 4-(nonadecylaminobenzoyl)-, 4-[p-[(1-methylpentadecyl)amino]benzoyl]-, and 4-[p-[(15-methylhexadecyl)amino]benzoyl]-butyrate esters, respectively.

EXAMPLE 21

Diethyl 2-p-(Hexadecylamino)benzoylglutarate

To a mixture of 16.0 g. of diethyl glutarate and 18.0 g. of N-trifluoroacetyl-p-(hexadecylamino)benzoyl chloride in 25 ml. of 1,2-dimethoxyethane under argon is added 2.0 g. of sodium hydride. The reaction mixture is refluxed for 5 hours, cooled, and poured onto ice. The mixture is then stirred an additional 5 hours, maintaining an alkaline pH with sodium hydroxide. The reaction mixture is then extracted with ether and the ether solution washed with water, saturated sodium chloride solution and dried over anhydrous sodium sulfate. The ether is then removed to yield the crude product. The pure product is obtained by chromatography on silica gel followed by crystallization from methylene chloride.

By employing an equimolar amount of N-trifluoroacetyl-p-(octylamino)benzoyl chloride, N-trifluoroacetyl-p-(dodecylamino)benzoyl chloride, N-trifluoroacetyl-p-(pentadecylamino)benzoyl chloride, N-trifluoroacetyl-p-(nonadecylamino)benzoyl chloride, N-trifluoroacetyl-p-[(1-methylpentadecyl)amino]benzoyl chloride and N-trifluoroacetyl-p-[(15-methylhexadecyl)amino]benzoyl chloride instead of the N-trifluoroacetyl-p-(hexadecylamino)benzoyl chloride of the preceding paragraph, there is obtained the diethyl 2-(p-ocylaminobenzoyl)-, 2-(dodecylaminobenzoyl)-, 2-(p-pentadecylaminobenzoyl)-, 2-(p-nonadecylaminobenzoyl)-, 2-[p-[(1-methylpentadecyl)amino]benzoyl]-, and 2-[p-[(15-methylhexadecyl)amino]benzoyl]- glutarate esters, respectively.

EXAMPLE 22

Diethyl 2-p-(Hexadecylamino)benzoylsuccinate

To a mixture of 15.6 g. of diethyl succinate and 18.0 g. of N-trifluoroacetyl-p-(hexadecylamino)benzoyl chloride in 25 ml. of 1,2-dimethoxyethane under argon is added 2.0 g. of sodium hydride. The reaction mixture is refluxed for 5 hours, cooled, and poured onto ice. The mixture is then stirred an additional 5 hours, maintaining an alkaline pH with sodium hydroxide. The reaction mixture is then extracted with ether and the ether solution washed with water, saturated sodium chloride solution, and dried over anhydrous sodium sulfate. The ether is then removed to yield the crude product. The pure product is obtained by chromatography over silica gel followed by crystallization from methylene chloride.

By following an equimolar amount of N-trifluoroacetyl-p-(octylamino)benzoyl chloride, N-trifluoroacetyl-p-(dodecylamino)benzoyl chloride, N-trifluoroacetyl-p-(pentadecylamino)benzoyl chloride, N-trifluoroacetyl-p-(octadecylamino)benzoyl chloride, N-trifluoroacetyl-p-[(1-methylpentadecyl)amino]benzoyl chloride, and N-trifluoroacetyl-p-[(15-methylhexadecyl)amino]benzoyl chloride instead of the N-trifluoroacetyl-p-(hexadecylamino)benzoyl chloride above, there is obtained the diethyl 2-(p-octylaminobenzoyl)-, 2-(p-dodecylaminobenzoyl(-, 2-(p-pentadecylaminobenzoyl)-, 2-(p-octadecylaminobenzoyl)-, 2-[p-[(1-methylpentadecyl)amino]benzoyl]-, and 2-[p-[(15-methylhexadecyl) amino]benxoyl]-succinate esters, respectively.

EXAMPLE 23

Preparation of N-carbobenzyloxy-4-(hexadecylamino)benzoyl chloride

To 15 g. of 4-(hexadecylamino)benzoic acid in 200 ml. water chloroform is added 15 g. sodium carbonate in 150 ml. water. To the vigorously stirred solution is added 10 g. carbobenzoyl chloride. After 2 hours stirring at 40° C., the layers are separated, washed three times with 1N hydrochloric acid, dried, and evaporated to an oil. The oil is dissolved in 300 ml. toluene, treated with 15 ml. of thionyl chloride, and the solution is refluxed for 5 hours. The solvents are evaporated and the residue is dissolved three times in toluene evaporating each time to yield a viscous, orange oil.

EXAMPLE 24

Preparation of Diethyl 4-(hexadecylamino)benzoylmalonate

To a warm solution of N-carbobenzoyloxy-N-(4-hexadecylamino)benzoyl chloride in 100 ml. ether is added a solution of 30.1 g. of sodium diethylmalonate in 20 ml. of 1,2-dimethoxyethane. An immediate precipitate forms, but the mixture is refluxed for one hour and filtered while hot. The solid is washed several times with hot ether, then the ether is evaporated to yield a white solid. The product is dissolved in tetrahydrofuran (100 ml.) and hydrogenated over 600 mg. 10% Pd-on-carbon at 50 pssi. until hydrogen up-take stops. The catalyst is filtered off. The solution is evaporated, and the residue is crystallized from acetic acid to yield the title compound as a crystalline mass.

EXAMPLE 25

Preparation of N-(t-butyloxycarbonyl)-4-(n-hexadecylamino)benzoylimidazole

A solution of 10 g. of 4-(n-hexadecylamino)benzoic acid in 100 ml. dioxane is treated with 4.0 g. of t-butylazidoformate and 10 ml. pyridine. After stirring at room temperature for 18 hours, the protected amidoacid is precipitated from solution by addition of 150 ml. of water. The product is collected and thoroughly dried. The crude product is dissolved in 200 ml. of a mixture consisting of methylene chloride/dimethoxyethane/pyridine (1:4:1), and to this is added 5.4 g. of 1,1'-carbonyldimidazole. The solution is stirred overnight at room temperature and the solvents are evaporated to yield the title compound as a thick, orange oil.

EXAMPLE 26

Preparation of Ethyl 2-p-hexadecylaminobenzoylacetoacetate

A solution of 21.6 g. of ethyl acetoacetate and 10 ml. of 1,2-dimethoxyethane (DME) is added to a suspension of 4.0 g. of sodium hydride in DME under argon. A solution of 17.3 g. of 1-[N-t-butyloxycarbonyl-p-(hexadecylamino)benzoyl]-imidazole in DME is then added. The reaction mixture is refluxed for 5 hours, cooled, poured on ice and extracted with ether. The ether solution is washed with water saturated sodium chloride solution, dried over anhydrous sodium sulfate and concentrated to dryness. The residue is heated for 30 minutes at 40° C. in 50 ml. of anhydrous trifluoroacetic acid. The solvent is again evaporated and the oil is crystallized from acetone to yield ethyl 2-p-(hexadecylamino)-benzoylacetoacetate.

EXAMPLE 27

Preparation of t-Butyl ethyl p-[(N-trifluoroacetyl N-hexadecyl)amino]benzoyl malonate In 125 ml. of 1,2 dimethoxyethane (DME) is suspended 926 mg. of sodium hydride, previously washed with hexane. To this suspension is added 4.0 g. of ethyl t-butyl malonate in 5 ml. of DME. The mixture is stirred an additional 15 min. after hydrogen evolution ceases. To this mixture is then added a solution of 5.0 g. p-(N-hexadecyl N-trifluoroacetylamino)benzoyl chloride in 15 ml. of DME. The reaction is stirred for 3 hours, poured on 100 g. of ice, acidified with hydrochloric acid and extracted into ether. The ether solution is washed with saturated sodium chloride solution, water, and dried over magnesium sulfate. Concentration of the ether solution by distillation yields the product.

By employing an equimolar amount of p-(N-octyl N-trifluoroacetylamino benzoyl chloride, p-(N-dodecyl N-trifloroacetylamino)benzoyl chloride, p-(N-pentadecyl N-trifluoroacetylamino)benzoyl chloride, p-{[(1-methylpentadecyl) N-trifluoroacetyl]amino}benzoyl chloride and p-{[(15-methyl hexadecyl)N-trifluoroacetyl]amino} benzoyl chloride instead of p-(N-hexadecyl N-trifluoroacetylamino)benzoyl chloride there is obtained the t-butyl ethyl p-(N-trifluoroacetyl N-octylamino)benzoyl, p-(N-trifluoroacetyl N dodecylamino)- benzoyl, p-(N-trifluoroacetyl N-pentadecylamino)benzoyl, p-[(1-methylpentadecyl)N-trifluoroacetylamino]benzoyl and p-[(15-methylhexadecyl)N-trifluoroacetylamino]benzoyl malonate esters respectively.

EXAMPLE 28

Preparation of Ethyl p-(hexadecylamino)benzoyl acetate

To 20 ml. of trifluoroacetic acid is added 4.0 g. of t-butyl ethyl p-[(N-trifluoroacetyl N-hexadecyl)amino]-benzoyl malonate. This mixture is heated to reflux for 1 hour. Reaction mixture is cooled and concentrated to a liquid. The liquid is dissolved in methylene chloride, extracted with water and the methylene chloride solution dried over magnesium sulfate. The solution is filtered and concentrated in vacuo to afford 3.6 g. of liquid. To this liquid residue is added 25 ml. of ethanol followed by methylene chloride until solution occurs. To this solution is added 7 ml. of 1N sodium hydroxide which is stirred at room temperature for 30 minutes and then cooled to give crystals. Filtration and recrystallization from ethanol gives the product.

By employing an equimolar amount of t-butyl ethyl p-[(N-trifluoroacetyl N-octyl)amino]benzoyl malonate, t-butyl ethyl p-[(N-trifluoroacetyl N-dodecyl)amino]-benzoyl malonate, t-butyl ethyl p-[(N-trifluoroacetyl N-pentadecyl)amino]benzoyl malonate, t-butyl ethyl p-{[(1-methylpentadecyl)N-trifluoroacetyl]amino}-benzoyl malonate, and t-butyl ethyl p-{[(15-methylhexadecyl)N-trifluoroacetyl]amino}benzoyl malonate instead of t-butyl ethyl p-[(N-trifluoroacetyl N-hexadecyl)amino]benzoyl malonate, there is obtained the ethyl p-(octylamino)benzoyl, p-(dodecylamino)benzoyl, p-(pentadecylamino)benzoyl, p-[(1-methylpentadecyl)amino]benzoyl and p-[(15-methylhexadecyl)amino]benzoyl acetate esters, respectively.

EXAMPLE 29

Preparation of 13,13-dimethyltetradecyl bromide

A solution of t-butylmagnesium bromide is prepared by reacting 13.7 g. of t-butyl bromide with 2.67 g. of magnesium turnings in 50 ml. dry tetrahydrofuran. The solution of Grignard reagent is dropwise added to a stirred, cold (−10° C.) solution of 36.1 g. of 1,12-dibromododecane and 0.2 g. of $Li_2CuCl_4$ in 75 ml. dry tetrahydrofuran at a rate such that the reaction temperature does not exceed −5° C. After one additional hour of stirring at −10° C., the solvent is evaporated and the resultant liquid is fractionated in vacuo to yield 13,13-dimethyltetradecyl bromide as a colorless liquid.

EXAMPLE 30

Preparation of ethyl 4-(13,13-dimethyltetradecyl)aminobenzoate

A solution of 10 g. of 13,13-dimethyltetradecyl bromide and 10.8 g. of ethyl 4-aminobenzoate in 75 ml. hexamethylphosphoramide is heated at 110° C. for 17 hours. The cooled solution is diluted with 100 ml. water, filtered, and the residue is washed in portions with 100 ml. 50% ethanol-water. After drying, the product is crystallized from ethanol-water. After drying, the product is crystallized from ethanol to yield ethyl 4-(13,13-dimethyltetradecyl)aminobenzoate as colorless crystals.

EXAMPLE 31

Preparation of 4-(13,13-dimethyltetradecyl)aminobenzoic acid

A solution of 5 g. of ethyl 4-(13,13-dimethyltetradecyl)aminobenzoate in 75 ml. 95% ethanol is saponified with 2.5 g. of 85% potassium hydroxide by refluxing for 5 hours. The warm solution is diluted with 150 ml. water and adjusted to pH 5 with 37% hydrochloric acid. The precipitate is filtered, washed with water, dried in vacuo and crystallized from acetic acid to yield the title compound as a creamcolored, amorphous solid.

EXAMPLE 32

Preparation of 14-methylpentadecyl bromide

By a procedure analogous to that described in Example 1, 3-methylbutylmagnesium bromide in tetrahydrofuran is reacted with 34.5 g. of 1,11-dibromoundecane and 0.2 g. of $Li_2CuCl_4$ in 75 ml. tetrahydrofuran. After one hour stirring at −10° C., the solution is evaporated and the resultant oil is distilled in vacuo to yield the colorless 14-methyl pentadecyl bromide.

EXAMPLE 33

Preparation of ethyl 4-(14-methylpentadecyl)aminobenzoate

A solution of 10 g. of 14-methylpentadecyl bromide and 10.8 g. of ethyl 4-aminobenzoate in 75 ml. hexamethylphosphoramide is heated at 120° C. for 17 hours. The cooled solution is diluted with 100 ml. water, filtered, and the residue is washed with 100 ml. 50% ethanol-water. The product is dried, then crystallized from ethanol to yield ethyl 4-(14-methylpentadecyl)aminobenzoate as colorless crystals.

EXAMPLE 34

Preparation of 4-(14-methylpentadecyl)aminobenzoic acid

A 4 g. sample of ethyl 4-(14-methylpentadecyl)aminobenzoate is hydrolized with 2.0 g. of 85% potassium hydroxide in 60 ml. 95% ethanol by refluxing the solution for 5 hours. The solution is cooled, diluted with 100 ml. water, and acidified to pH 4.5 with 37% hydrochloric acid. The precipitate is collected and dried in vacuo to yield the title compound as a white powder.

EXAMPLE 35

Preparation of 15-methylhexadecyl bromide

A solution of 3-methylbutylmagnesium bromide is prepared by treating 15.1 g. of 3-methylbutyl bromide with 2.7 g. of magnesium turnings in 50 ml. dry tetrahydrofuran. The resultant Grignard reagent is dropwise added to a cold (−10° C.) solution of 36.1 g. of 1,12-dibromododecane and 0.2 g. of $Li_2CuCl_4$ in 75 ml. dry tetrahydrofuran. The solution is stirred for 1 hour, evaporated, and fractionally distilled in vacuo to yield 15-methylhexadecyl bromide as a colorless liquid.

EXAMPLE 36

Preparation of ethyl 4-(15-methylhexadecyl)aminobenzoate

A mixture of 5 g. of 15-methylhexadecyl bromide and 5.2 g. of ethyl 4-aminobenzoate in 50 ml. hexamethylphosphoramide is heated for 17 hours at 120° C. The cooled solution is diluted with an equal volume of water and the resultant precipitate is filtered, washed with 100 ml. of 50% ethanol, dried, and crystallized from ethanol to yield a colorless crystalline solid.

EXAMPLE 37

Preparation of 4-(15-methylhexadecyl)aminobenzoic acid

A solution of 3.5 g. of ethyl 4-(15-methylhexadecyl)aminobenzoate and 1.7 g. of 85% potassium hydroxide in 50 ml. of 95% ethanol is heated at reflux for 5 hours. The warm solution is diluted with 100 ml. water and adjusted to pH5 with 37% hydrochloric acid. The precipitate is collected, dried, and crystallized from acetic acid to yield the title compound as an amorphous, cream-colored solid.

EXAMPLE 38

Preparation of 11-Oxo-15,15-dimethylhexadecyl bromide

An ether solution of 4,4-dimethylpentylmagnesium bromide is prepared from 35 g. (0.195 mmoles) 1-bromo-4,4-dimethyl pentane (prepared by bubbling isobutylene through a solution of 3-bromopropanol in concentrated sulfuric acid) and 5.2 g. magnesiym turnings in 100 ml. anhydrous ether. After refluxing the Grignard reagent for ½ hour, heating is removed and 17.9 g. (1 eq.) freshly dried cadmium chloride is added in portions. The solution is again refluxed for ½ hour, then the ether is distilled off and replaced by 200 ml. dry toluene. When the reaction temperature has reached 80° C., heating is removed and 27.7 g. (97.5 mmoles) 11-bromoundecanoyl chloride is added in portions. Heating is continued for 45 minutes at 100°, the solution is cooled and mixed with 200 ml. 10% sulfuric acid-water. After most of the salts have dissolved, the layers are separated, and the aqueous layer is extracted twice with ether. The organic solutions are washed with saturated sodium bicarbonate and brine, dried and condensed to a yellow semi-solid mass. Distillation in vacuo yields the title compound as a colorless, low-melting waxy solid.

EXAMPLE 39

Preparation of Ethyl 4(11-oxo-15,15-dimethylhexadecyl)aminobenzoate

A solution of 15 g. (43.2 mmoles) 11-oxo-15,15-dimethylhexadecyl bromide and 14.3 g. (2 eq.) ethyl 4-aminobenzoate in 100 ml. hexamethylphosphoramide is heated at 120° C. for 18 hours. The cooled solution is diluted with 200 ml. water and filtered. The resultant solid is washed in portions with 200 ml. 50% ethanol-water, dried, and crystallized from ethanol to yield a colorless, waxy solid.

EXAMPLE 40

Preparation of Ethyl 4(15,15-dimethylhexadecyl)amino benzoate

An ice-cold solution of 10 g. (23.2 mmoles) ethyl 4(11-oxo-15,15-dimethylhexadecyl)aminobenzoate in 100 ml. dry tetrahydrofuran is treated with 8.5 ml. (1.1 eq.) 1M borane tetrahydrofuran complex. The solution is heated 15 hours at 50° C., cooled, and mixed with 100 ml. 10% hydrochloric acid solution. This is extracted twice with 100 ml. ether, dried, and condensed to a colorless syrup.

A mixture of crude ethyl 4-(11-hydroxyO15,15-dimethylhexadecyl)aminobenzoate (23.2 mmoles) and 2.6 g. (1.1 eq.) triethylamine in 200 ml. methylene chloride is cooled to −15° C. in a dry ice-acetone bath. To the vigorously stirred solution is added 2.9 g. methanesulfonyl chloride in 25 ml. methylene chloride at a rate such that the reaction temperature does not exceed −10° C. After the methane sulfonyl chloride has been added, the reaction is allowed to warm to room temperature, then washed in sequence with 100 ml. of the following ice-cold solutions: water, 10% hydrochloric acid, saturated sodium bicarbonate, and brine. The dried organic solution is condensed to a viscous, orange oil.

The crude ethyl 4(11-methanesulfonyloxy-15,15-dimethylhexadecyl)aminobenzoate is dissolved in 30 ml. dry tetrahydrofuran and the reaction flask is flushed with argon. To this is added 49 ml. 1 M lithium triethylborohydride in tetrahydrofuran, and the solution is stirred at 50° C. for 17 hours. The reaction is then cooled and treated in sequence with 10 ml. 5N sodium hydroxide and 16 ml. 30% hydrogen peroxide solutions. The mixture is poured into 300 ml. water and extracted three times with 100 ml. portions of methylene chloride. The organic layers are combined, dried, and condensed to a viscous oil, crystallization from ethanol yields the title compound as a white, crystalline mass.

EXAMPLE 41

Preparation of 4-(15,15-dimethylhexadecyl)aminobenzoic acid

A solution of 5 g. (12 mmoles) ethyl 4–15,15-dimethylhexadecyl)aminobenzoate and 2.4 g. (3 eq.) 85% potassium hydroxide in 50 ml. 95% ethanol is heated at 80° C. for 4 hours. The solution is diluted with 100 ml. ethanol, acidified to pH-5 with 37% hydrochloric acid, filtered, and the white precipitate is washed with water. Drying, followed by crystallization from acetic acid yields the title compound as white crystals.

EXAMPLE 42

Preparation of 50 mg. Tablets

| Per Tablet | | Per 10,000 Tablets |
|---|---|---|
| 0.050 gm. | p(Hexadecylamino)benzoyl-acetonitrile | 500 gm. |
| 0.080 gm. | Lactose | 800 gm. |
| 0.010 gm. | Corn Starch (for mix) | 100 gm. |
| 0.008 gm. | Corn Starch (for paste) | 75 gm. |
| 0.148 gm. | | 1475 gm. |
| 0.002 gm. | Magnesium Stearate (1%) | 15 gm. |
| 0.150 gm. | | 1490 gm. |

The p-(hexadecylamino)benzoylacetonitrile, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dry granules are then passed through a No. 16 screen. The mixture is lubricated with 1% magnesium stearate and compressed into tablets in a suitable tableting machine.

EXAMPLE 43

Preparation of Oral Suspension

| Ingredient | Amount |
|---|---|
| Diethyl p-(hexadecylamino)benzoylmalonate | 500 mg. |
| Sorbitol solution (70% N.F.) | 40 ml. |
| Sodium benzoate | 150 mg. |
| Saccharin | 10 mg. |
| Red dye | 10 mg. |
| Cherry flavor | 50 mg. |
| Distilled water qs ad | 100 ml. |

The sorbitol solution is added to 40 ml. of distilled water and the diethyl p-(hexadecylamino)benzoylmalonate is suspended therein. The saccharin, sodium benzoate, flavor and dye are added and dissolved. The volume is adjusted to 100 ml. with distilled water. Each ml. of syrup contains 5 ml. of diethyl p-(hexadecylamino)benzoylmalonate.

I claim:

1. A compound selected from the group consisting of those of the formula:

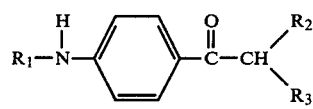

and the enol tautomers thereof wherein $R_1$ is an unbranched or branched alkyl group of the formula $C_nH_{2n+1}$ wherein n is an integer from 8 to 19, inclusive; $R_2$ is selected from the group consisting of carboxy, carbamoyl, cyano, lower alkoxycarbonyl having up to 4 carbon atoms in the alkoxy moiety, lower alkylsulfonyl having up to 4 carbon atoms, lower alkylsulfinyl having up to 4 carbon atoms, arylsulfonyl, arylsulfinyl, lower alkanoyl having up to 4 carbon atoms, benzoyl, monosubstituted benzoyl, lower alkoxycarbonylalkyl having up to 4 carbon atoms in each of the alkyl and alkoxy moieties and lower carboxyalkyl having up to 4 carbon atoms; and $R_3$ is selected from the group consisting of hydrogen, cyano, lower alkyl carbamoyl having up to 4 carbon atoms, lower alkoxycarbonyl having up to 4 carbon atoms, lower alkylsulfonyl having up to 4 carbon atoms, lower alkylsulfinyl having up to 4 carbon atoms, arylsulfonyl, arylsulfinyl, lower alkanoyl having up to 4 carbon atoms, benzoyl, monosubstituted benzoyl, lower alkoxycarbonylalkyl having up to 4 carbon atoms in each of the alkyl and alkoxy moieties and lower carboxyalkyl having up to 4 carbon atoms; and the pharmacologically acceptable acid-addition and cationic salts thereof.

2. A compound selected from the group consisting of those of the formula

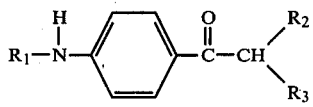

and the enol tautomers thereof wherein $R_1$ is an unbranched or branched alkyl group of the formula $C_nH_{2n+1}$ wherein n is an integer from 8-19, inclusive; $R_2$ is selected from the group consisting of cyano, carbamoyl, methoxycarbonyl, ethoxycarbonyl, carboxy, methanesulfonyl, ethanesulfonyl, phenylsulfonyl, methanesulfinyl, ethaneshulfinyl, phenylsulfinyl, benzoyl, acetyl, propionyl, butyryl, lower alkoxycarbonylmethyl having up to 4 carbon atoms in the alkoxy moiety, lower alkoxycarbonylethyl having up to 4 carbon atoms in the alkoxy moiety, lower alkoxycarbonylpropyl having up to 4 carbon atoms in the alkoxy moiety, lower alkoxycarbonylbutyl having up to 4 carbon atoms in the alkoxy moiety, carboxymethyl, carboxyethyl, carboxypropyl and carboxybutyl; and $R_3$ is selected from the group consisting of hydrogen, cyano, methoxycarbonyl, ethoxycarbonyl, carboxy, methanesulfonyl, ethanesulfonyl, phenylsulfonyl, methanesulfinyl ethanesulfinyl, phenylsulfinyl, benzoyl, acetyl, propionyl, butyryl, lower alkoxycarbonylmethyl having up to 4 carbon atoms in the alkoxy moiety, lower alkoxycarbonylethyl having up to 4 carbon atoms in the alkoxy moiety, lower alkoxycarbonylpropyl having up to 4 carbon atoms in the alkoy moiety, lower alkoxycarbonylbutyl having up to 4 carbon atoms in the alkoxy moiety, carboxymethyl, carboxyethyl, carboxypropyl and carboxybutyl; and the pharmacologically acceptable acid-addition and cationic salts thereof.

3. A compound selected from the group consisting of those of the formula:

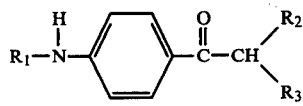

and the enol tautomers thereof wherein $R_1$ is an unbranched or branched alkyl group of the formula $C_nH_{2n+1}$ wherein n is an integer from 13–17, inclusive; $R_2$ is selected from the group consisting of carbamoyl, cyano, methoxycarbonyl, ethoxycarbonyl, carboxy, methanesulfonyl, phenylsulfonyl, methanesulfinyl, phenylsulfinyl, benzoyl, acetyl, propionyl, lower alkoxycarbonylmethyl having up to 4 carbon atoms in the alkoxy moiety, lower alkoxycarbonylethyl having up to 4 carbon atoms in the alkoxy moiety, carboxymethyl and carboxyethyl; and $R_3$ is selected from the group consisting of hydrogen, cyano, methoxycarbonyl, ethoxycarbonyl, methanesulfonyl, phenylsulfonyl, methanesulfinyl, phenylsulfinyl, benzoyl, acetyl, propionyl, lower alkoxycarbonylmethyl having up to 4 carbon atoms in the alkoxy moiety, lower alkoxycarbonylethyl having up to 4 carbon atoms in the alkoxy moiety, carboxymethyl and carboxyethyl; and the pharmacologically acceptable acid-additon and cationic salts thereof.

4. The compound according to claim 1 wherein n is 16, $R_2$ is cyano, and $R_3$ is hydrogen; p-(hexadecylamino)benzoylacetonitrile.

5. The compound according to claim 1 wherein n is 16, $R_2$ and $R_3$ are ethoxycarbonyl: diethyl p-(hexadecylamino)benzoylmalonate.

6. The compound according to claim 1 wherein n is 16, $R_2$ is cyano, and $R_3$ is ethoxycarbonyl: ethyl 2-cyano-2-(p-hexadecylaminobenzoyl)acetate.

7. The compound according to claim 1 wherein n is 16, $R_2$ is acetyl, and $R_3$ is ethoxycarbonyl: ethyl p-(hexadecylamino)benzoylacetoacetate.

8. The compound according to claim 1 wherein n is 16, $R_2$ is carboxy and $R_3$ is hydrogen: p-(hexadecylamino)benzoylacetic acid.

9. The compound according to claim 1 wherein n is 16, $R_2$ is methanesulfonyl and $R_3$ is hydrogen: 4'-hexadecylamino-2-(methylsulfonyl)acetophenone.

10. The compound according to claim 1 wherein n is 16, $R_2$ is methanesulfinyl and $R_3$ is hydrogen: 4'-hexadecylamino-2-(methylsulfinyl)acetophenone.

11. The compound according to claim 1 wherein n is 16, $R_2$ is phenylsulfonyl and $R_3$ is hydrogen: 4'-hexadecylamino-2-(phenylsulfonyl)acetophenone.

12. The compound according to claim 1 wherein n is 16, $R_2$ is phenylsulfinyl and $R_3$ is hydrogen: 4'-hexadecylamino-2-(phenylsulfinyl)acetophenone.

13. The compound according to claim 1 wherein n is 16, $R_2$ and $R_3$ are acetyl: 3-p(hexadecylamino)benzoyl-2,4-pentanedione.

14. The compound according to claim 1 wherein n is 16, $R_2$ is ethoxycarbonyl and $R_3$ is benzoyl: ethyl 2-benzoyl-2-(p-hexadecylaminobenzoyl)acetate.

15. The compound according to claim 1 wherein n is 16, $R_2$ is methylenecarboxy and $R_3$ is hydrogen: 3-p-hexadecylamino)benzoylpropionic acid.

16. The compound according to claim 1 wherein n is 16, $R_2$ is ethylenecarboxy and $R_3$ is hydrogen: 4-p-(hexadecylamino)benzoylbutyric acid.

17. The compound according to claim 1 wherein n is 16, $R_2$ is methyleneethoxycarbonyl and $R_3$ is hydrogen: ethyl 3-p-(hexadecylamino)benzoylpropionate.

18. The compound according to claim 1 wherein n is 16, $R_2$ is ethyleneethoxycarbonyl and $R_3$ is hydrogen; ethyl 4-p-(hexadecylamino)benzoylbutyrate.

19. The compound according to claim 1 wherein n is 16, $R_2$ is ethyleneethoxy carbonyl and $R_3$ is ethoxycarbonyl: diethyl 2-p-(hexadecylamino)benzoylabutarate.

20. The compound according to claim 1 wherein n is 16, $R_2$ is ethoxycarbonyl and $R_3$ is hydrogen: ethyl p-(hexadecylamino)benzoylacetate.

21. The compound according to claim 1 wherein n is 16, $R_2$ is methyleneethoxycarbonyl and $R_3$ is ethoxycarbonyl: diethyl 2-p-(hexadecylamino)benzoylsuccinate.

* * * * *